(12) United States Patent
Martens

(10) Patent No.: US 7,657,163 B2
(45) Date of Patent: Feb. 2, 2010

(54) FLUID WARMING SYSTEM AND TECHNIQUE FOR USING THE SAME

(75) Inventor: Paul W Martens, Pleasanton, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 375 days.

(21) Appl. No.: 11/527,069

(22) Filed: Sep. 26, 2006

(65) Prior Publication Data
US 2008/0077087 A1 Mar. 27, 2008

(51) Int. Cl.
*F24F 3/14* (2006.01)
*A61N 1/30* (2006.01)
(52) U.S. Cl. .................................... 392/470
(58) Field of Classification Search ........... 392/470, 392/465–496; 604/19–114
See application file for complete search history.

(56) References Cited

U.S. PATENT DOCUMENTS

| 4,626,666 A * | 12/1986 | Maeda et al. ............... 219/537 |
| 2003/0176903 A1 * | 9/2003 | Park ........................... 607/106 |
| 2005/0067406 A1 * | 3/2005 | Rajarajan et al. ............ 219/553 |
| 2005/0148934 A1 * | 7/2005 | Martens et al. ............. 604/113 |
| 2008/0045910 A1 * | 2/2008 | Chau ........................... 604/291 |

FOREIGN PATENT DOCUMENTS

WO 0016839 3/2000

* cited by examiner

*Primary Examiner*—Daniel L Robinson
(74) *Attorney, Agent, or Firm*—Fletcher Yoder

(57) ABSTRACT

A fluid warming device for warming medical fluids, such as intravenously administered blood or saline solutions, is provided. The fluid warming device includes a conduit at least partially formed from a material with positive temperature coefficient properties. A supply of blood or other fluids may pass through the device and be heated to temperatures appropriate for administration to a patient.

24 Claims, 3 Drawing Sheets

FLUID WARMING SYSTEM AND TECHNIQUE FOR USING THE SAME

BACKGROUND OF THE INVENTION

1. Field of the Invention

The present invention relates generally to medical devices and, more particularly, to fluid warming devices designed for medical applications.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Fluids that are administered intravenously to a patient typically include blood-based fluids and non-blood fluids, all referred to as "IV fluids." IV fluids may include whole blood, serum, plasma, blood substitutes, electrolytes, and/or therapeutic compounds, for example. While patient body temperatures are generally in the range of 36° C. to 38° C., IV fluids are often stored at much colder temperatures. For example, transfusable human blood is typically stored at temperatures from about 4° C. to about 10° C., while non-blood fluids, such as saline, are typically stored at room temperature. In order to reduce changes in patient temperature resulting from IV fluid administration, healthcare workers generally warm IV fluids prior to their administration to a patient.

Often, IV fluids are warmed in a water bath or other heating device prior to administration. However, as the IV fluids are transferred from the water bath to patient, there may be heat loss through both radiation and convection caused by the distance and the length of time of the fluid transfer. An additional disadvantage of using a water bath to warm IV fluids is that the temperature of the bath must be accurately maintained at the desired temperature to ensure proper heating of the IV fluids and a water bath may take a considerable amount of time to heat a fluid. Therefore, in order to consistently heat fluids to the correct temperature, the temperature of the water may need to be frequently measured to ensure that bath will not cause IV fluids to be overheated, which may affect the integrity of certain components of the fluids, or underheated, which may affect solubility of electrolytes or therapeutic compounds in the fluids. Further, water baths may need to be regularly cleaned in order to prevent microbial contamination of the water.

Other warming devices may include medical tubing with a built-in water bath. Such devices typically have an outer lumen that surrounds the tube and that carries warm water that warms IV fluids flowing through an inner lumen. Such devices may partially reduce temperature loss caused by fluid transfer to the patient, as the tubing may simultaneously transport and warm an IV fluid. However, as the warming mechanism is a water bath, many of the associated disadvantages persist. For example, the reservoir supplying the warmed water may become contaminated. Additionally, the temperature of the water reservoir may need to be closely monitored to ensure that the water flowing through the tubing is the correct temperature.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a conduit for transferring a medical fluid, wherein the conduit includes at least one portion configured to heat the medical fluid to approximately body temperature via a positive temperature coefficient material.

There is also provided a fluid warming system that includes: a conduit adapted to be connected to a medical fluid supply, wherein the conduit includes at least one portion configured to heat the medical fluid to approximately body temperature via a positive temperature coefficient material; and a controller operatively connected to the conduit, wherein the controller provides sufficient current to the positive temperature coefficient material to heat the medical fluid to approximately body temperature.

There is also provided a method of warming a fluid that includes: transferring a fluid through a conduit comprising a positive temperature coefficient material; and applying sufficient current to the positive temperature coefficient material to heat the fluid to approximately body temperature.

There is also provided a method of manufacturing a fluid warming device that includes: providing a conduit for transferring a medical fluid, wherein the conduit includes at least one portion configured to heat the medical fluid to approximately body temperature via a positive temperature coefficient material.

There is also provided a method of administering a warmed fluid to a patient that includes transferring a fluid through a conduit comprising a positive temperature coefficient material such that the fluid is warmed to approximately body temperature; and administering the warmed fluid to the patient.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Provided herein are medical devices that are appropriate for fluid warming. A medical device for fluid warming according to the present techniques may be formed at least in part from a positive temperature coefficient material. A positive temperature coefficient material is characterized in that the material exhibits increased electrical resistance as a function of temperature. The use of positive temperature coefficient materials for IV fluid warming provides multiple advantages. For example, a positive temperature coefficient material may be at least partially temperature self-regulating as a result of its increased resistance in response to increased temperature, which may provide more reliable heating for IV fluids. Further, these materials provide "dry" heating and thus avoid some of the maintenance problems associated with IV fluid warming via water baths. Additionally, these materials may be integrated into an in-line system that warms an IV fluid en route to a patient. Such an in-line configuration allows the distance between the warming device and the patient to be minimized, which may reduce temperature loss associated with IV fluid transport.

Figure 1:
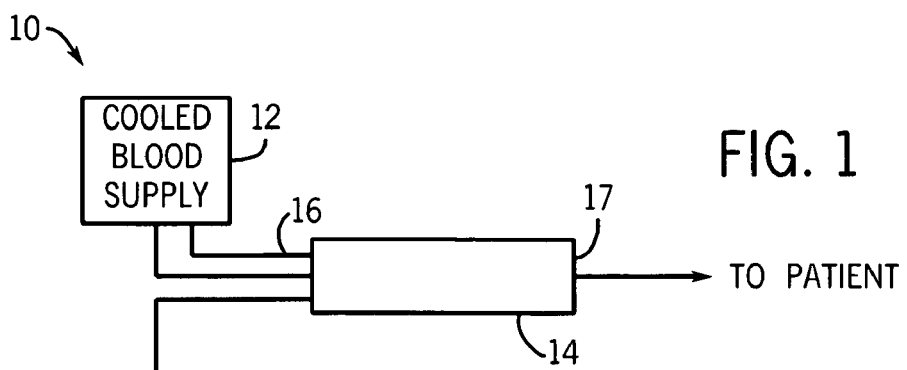
FIG. 1 illustrates a schematic of an exemplary fluid warming system according to the present techniques.

FIG. 1 illustrates a schematic view of an in-line fluid warming system 10 according to the present techniques. The system 10 may be used for the warming of a fluid prior to administration of the fluid to a patient. The system operatively connects a fluid supply 12 to a warming device 14 as provided herein. The warming device 14 includes an inlet 16 and an outlet 17. The inlet 16 is coupled to the fluid supply 12 such that the fluid passes into and through the warming device 14 before exiting through the outlet 17. The warming device 14 may be sized and shaped in order to suitably warm the IV fluid and substantially maintain a desired fluid temperature until the fluid is administered to the patient. For example, the warming device 14 may be integrated into all or part of the length of medical tubing that transfers the IV fluid from the fluid supply 12 to the patient. It is envisioned that the warming device 14 may range in size from several inches to several feet. In one embodiment, the warming device is at least 48 inches. After exiting the warming device 14 through the outlet 17, the warmed fluid may subsequently pass through a short stretch of tubing and/or a connector (not shown) and into a cannula (not shown) that is directly coupled to a patient's peripheral or central vein. In another embodiment, a fluid may be heated to a slightly higher temperature than body temperature and may be subsequently transferred through a length of tube where sufficient heat loss occurs to bring the fluid temperature down to body temperature. In certain embodiments, the system 10 is an IV gravity drip system, and the fluid is passively administered to the patient. In other embodiments, the system 10 includes an infusion pump (not shown) or other device that controls the rate of IV fluid administration to the patient.

A controller 18 supplies current to the warming device 14. In certain embodiments, the controller 18 may also include a microprocessor that processes information related to IV fluid temperature. Although the positive temperature coefficient material as provided herein may be temperature self-regulating, in certain embodiments it may be advantageous to provide back-up systems that sense fluid temperature and modify the current flow as desired. The controller 18 may include an input circuit configured to receive data (e.g., fluid temperature from a temperature sensor). Further, the controller 18 may include a memory storing an algorithm configured to calculate adjustments for inducing, maintaining, and/or controlling temperature of the fluid. Such algorithms (e.g., P, PD, PI, and PID algorithms) may be utilized to maintain the fluid at a desired temperature.

Figure 2:
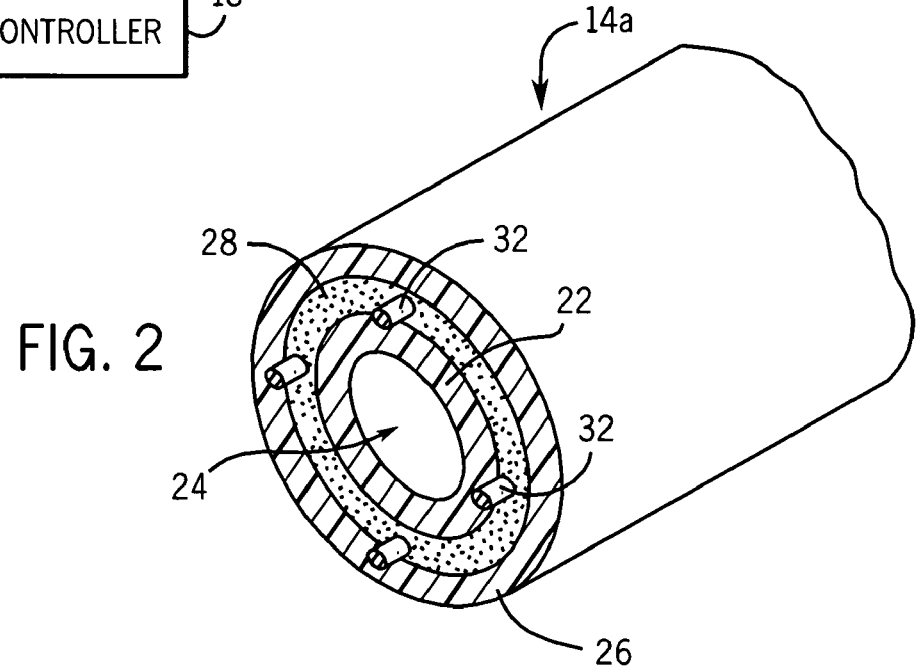
FIG. 2 illustrates a cross-sectional view of an exemplary warming device with a warming layer disposed between two structural layers.

FIG. 2 illustrates a cross-sectional view of an exemplary warming device 14a. As depicted in FIG. 2, the warming device 14a may be a generally tube-shaped structure that includes three layers. Specifically, the warming device 14a has an inner layer 22 defining a fluid-conveying passageway 24. The fluid-conveying passageway 24 may have an annulus diameter from about 0.005 to 0.500 inches, for example. The warming device 14a also includes an outer layer 26. The inner layer 22 and outer layer 26 substantially surround a warming layer 28, described in more detail below. The inner layer 22 and outer layer 26 may be formed from medical polyvinyl chloride or any other suitable material. Although the particular dimensions of the inner layer 22 and outer layer 26 are not critical, it is envisioned that in certain embodiments, the outer layer 26 may be relatively more insulating to prevent heat loss while the inner layer may be relatively less insulating in order to effectively transfer heat to the fluid in the passageway 24. Thus, in certain embodiments it may be advantageous for the outer layer 26 and the inner layer 22 to be constructed from different materials and/or have different thicknesses. In circumstances where it is desirable to preserve flexibility of the warming device 14a, the thickness of the inner layer 22 and the outer layer 26 may range from about 0.010 to 0.100 inches, for example. Further, the inner layer 22 and the outer layer 26 may be formed to allow thermal expansion of the warming layer 28. In such embodiments, it may be advantageous to form the inner layer 22 and the outer layer 26 from highly elastomeric materials or to construct the warming device 14a such that there is a gap between the warming layer 28 and the inner layer 22 and/or the warming layer 28 and the outer layer 26. In some embodiments, the warming layer 28 may be about 0.005 to 0.100 inches thick, and in specific embodiments, may be about 0.020 to 0.075 inches thick.

The warming layer 28 is formed from a positive temperature coefficient material. The warming layer 28 may include a plurality of electrically conductive bus wires 32 that are also embedded within and extend along the length of the warming layer 28. The conductive bus wires 32 are operatively connected with controller 18 (FIG. 1). As a fluid passes through the passageway 24 of the warming device 14a, the controller 18 supplies electrical current that passes through the conductive bus wires 32 to generate heat. The positive temperature coefficient material may be self-regulating and thus control the current delivered by the controller 18. The positive temperature coefficient material may include a network of conductive bodies embedded in a substrate, such as a polymer substrate. When a current is applied to the substrate, such as through the conductive bus wires 32, the temperature of the substrate rises, and the substrate undergoes a phase change, which generally involves expansion. The phase change of the substrate causes the embedded conductive bodies to lose contact with one another, thereby disrupting their conductive paths. As the network of conductive bodies is disrupted, the internal resistance of the material increases. At a predetermined equilibrium temperature or narrow temperature range, the resistance of the material is sufficiently high that the current flow is reduced to levels that maintain the temperature of the material without heating it any further. It is envisioned that that the equilibrium temperature for the positive temperature coefficient material may be a temperature that is sufficient to heat the fluid to approximately body temperature, generally 36° C. to 38° C. In certain embodiments, the equilibrium temperature may range from 35° C.-45° C. At temperatures substantially higher than the equilibrium temperature, the current flow is substantially eliminated, thus allowing the material to cool until the equilibrium temperature is reached. Such a temperature regulation cycle may remain in effect as long as current is being passed to the material, i.e. as long as the fluid warming system is switched on. In effect, the warming layer 28 may be thought of as having many variable resistors in parallel along its length. Each conductive path defined in the network of conductive bodies may be considered to be a self-regulated or autotherming circuit providing heat locally.

Figure 3:
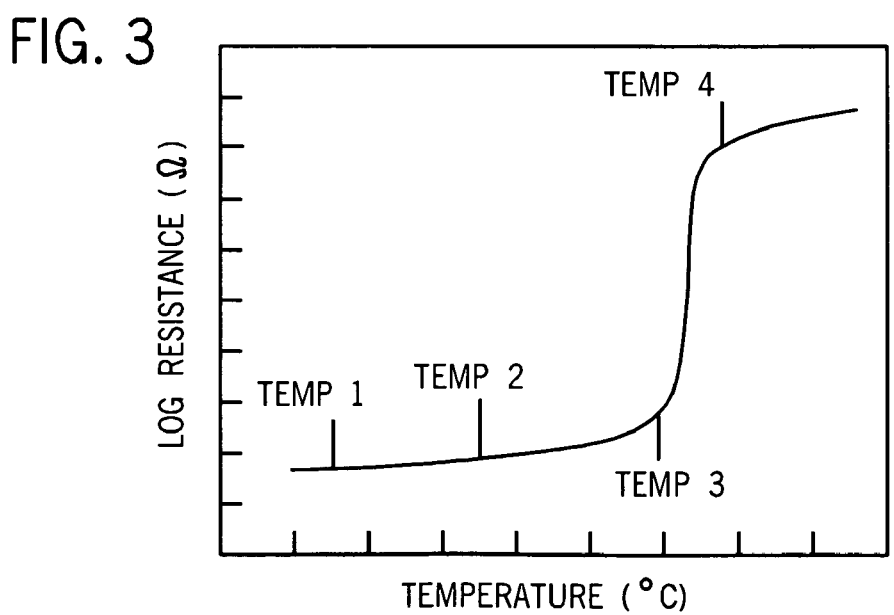
FIG. 3 is a hypothetical plot of the resistance of an exemplary positive temperature coefficient material versus temperature.

Several materials exhibit positive temperature coefficients, such as metals, certain ceramics, and certain polymers or semiconductive plastics, such as those available from Raychem (Menlo Park, Calif.). While metals may experience a linear relationship between resistance and temperature, engineered ceramics and polymers may have an exponential relationship between resistance and temperature within a relatively narrow temperature range. FIG. 3 illustrates an exemplary operating curve for a generic polymeric positive temperature coefficient material showing the relationship between the log of the resistance versus temperature. The transition temperature, or switching temperature, may be defined as the point at which the resistance-temperature characteristic begins to increase sharply, such as at Temperature 2 in FIG. 3. In certain embodiments, the transition temperature may be defined as the temperature at which the resistance is twice the base resistance, which is the resistance of the material at room temperature, or 25° C. At some point after Temperature 3, the resistance becomes so high as to substantially reduce or eliminate the current flow. At Temperature 4, the resistance of the material may be so high as to effectively be infinite. In certain embodiments, the transition temperature may range from 30° C.-45° C. In specific embodiments, the transition temperature may range from 35° C.-45° C.

The type of polymer as well as the type and concentration of conductive bodies in the positive temperature coefficient material may affect its properties. The warming layer 28 may be formed from a polymer such as polyethylene, polyvinyl chloride, polyester, polyurethane, polyimide, silicon and epoxy resins, thermal setting resins, or any combination thereof. For example, cross-linked polymers may be appropriate for use in the warming layer 28. In other embodiments, polymers with high melt points (e.g. greater than 90° C.), such as ethyl vinyl alcohols or low or high density polyethylene, may also be appropriate for use in the warming layer 28. Further, the warming layer 28 may include ethylene/ethyl acrylate copolymer and polyvinylidene fluoride, thermoplastic crystalline polymers such as olefin polymers, including homopolymers, polyalkenamers obtained by polymerizing cycloolefins; copolymers of two or more olefins, and copolymers of one or more olefins, e.g., ethylene or propylene, with one or more olefinically unsaturated comonomers, such as vinyl acetate, acrylic acid, methyl acrylate and ethyl acrylate, or fluoropolymers including copolymers of ethylene with tetrafluroethylene and/or a perfluoro-alkoxy comonomer. The conductive bodies embedded in the polymer can be in the form of particles or fibers and may include carbon, such as carbon black, coated carbon, graphite, coated graphite, metal, alloy and ceramic materials. In some embodiments, the positive temperature coefficient material includes electrically conductive bodies in the concentration of at least 0.5% to 50% by weight.

Figure 4:
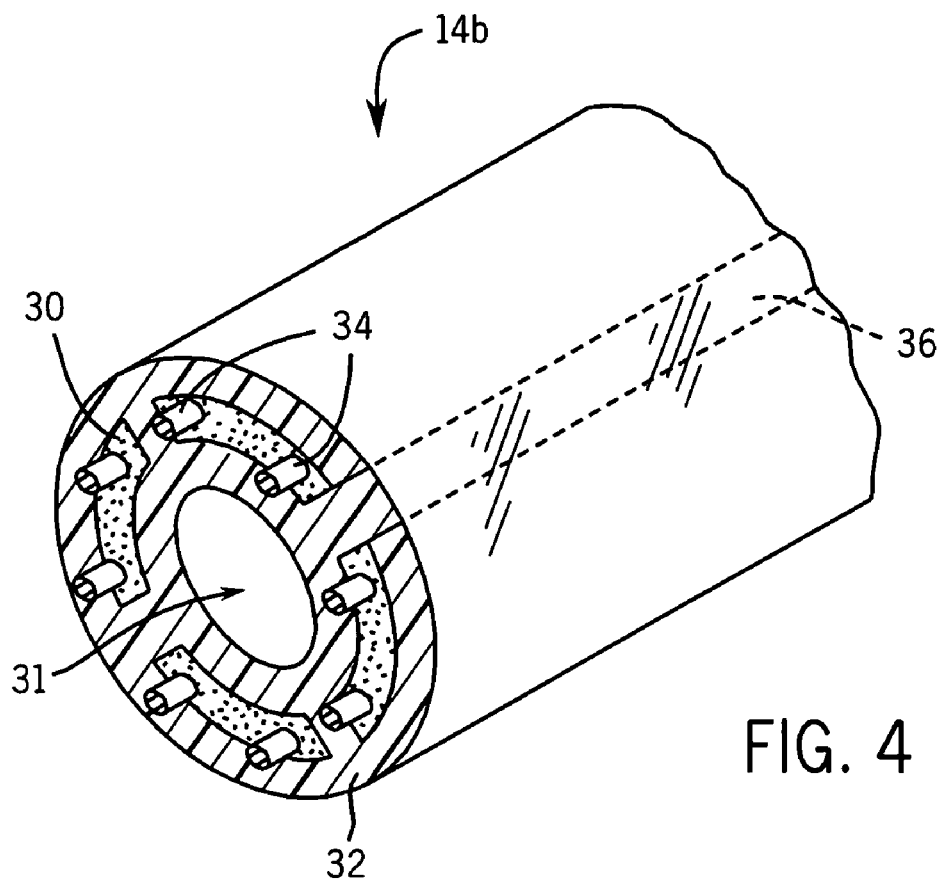
FIG. 4 illustrates a cross-sectional view of an exemplary warming device with warming sections embedded in a support substrate.

FIG. 4 illustrates an alternative configuration of a warming device 14b that includes four circumferentially spaced apart outward warming quadrants 30 embedded within a transparent or translucent substrate 32 that defines a fluid passageway 31. The warming quadrants 30 may each contain at least two bus wires 34 within a positive temperature coefficient material. The depicted arrangement provides multiple viewing windows 36. This configuration provides the advantage of allowing a healthcare worker to view the fluid as it flows through the warming device 14b.

Figure 5:
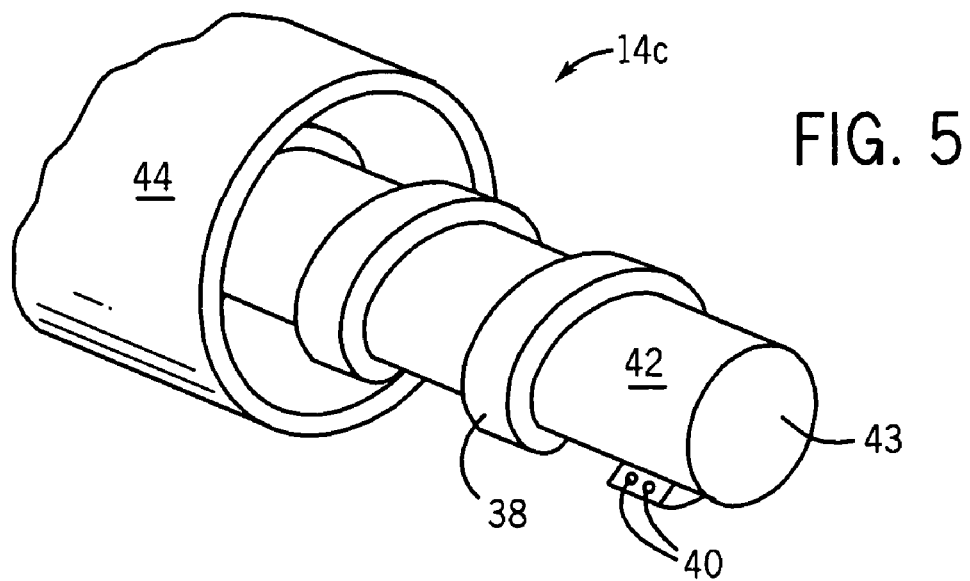
FIG. 5 illustrates a cross-sectional view of an exemplary warming device with a spiral warming element.

FIG. 5 illustrates an alternate warming device 14c that includes a warming element 38 that runs along the warming device 14c in a nonlinear fashion. In this embodiment, the warming element 38, which includes bus bars 40, is spirally wrapped around a polymer substrate layer 42 that defines the fluid-conveying passageway 43. This configuration may provide enhanced flexibility to the warming device 14c as the positive temperature coefficient heating elements and bus bars/wires may be relatively stiff compared to the polymer substrate layer 42. As the warming element 38 may be wrapped in a loose spiral, the polymer substrate layer 42 remains highly flexible in areas not covered by the warming element 38. Additionally, this configuration provides the advantage of minimizing the total amount of warming element 38 per inch of the warming device 14c to reduce total stiffness. The spiral configuration may also provide additional area for natural thermal expansion of the warming element 38. The warming device 14c may also include an insulating layer 44 for mechanical and electrical protection of the warming element 38.

Figure 6:
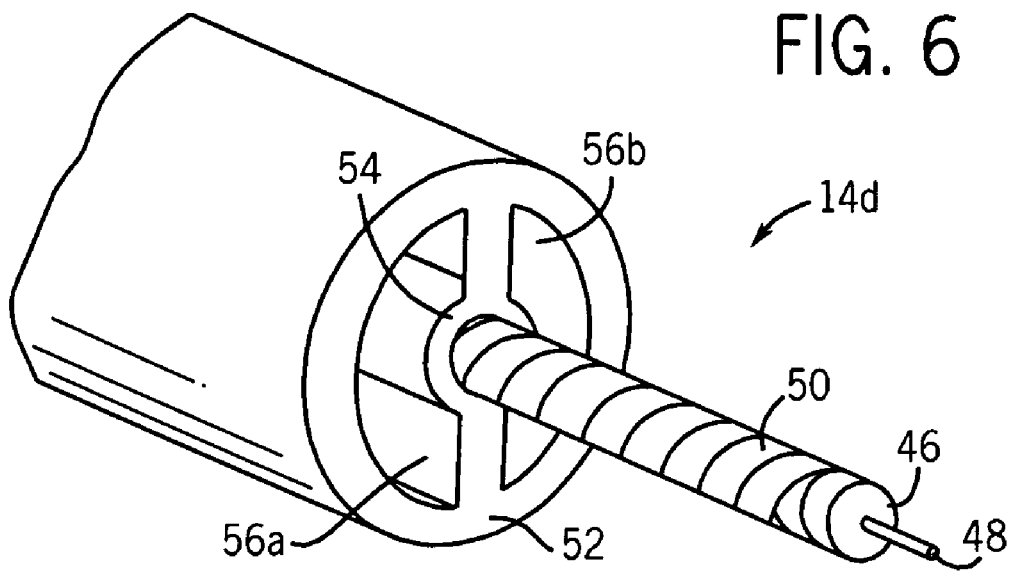
FIG. 6 illustrates a cross-sectional view of an exemplary warming device with an interior warming rod.

FIG. 6 illustrates an alternative configuration of a warming device 14d that may provide certain fluid heating advantages. As depicted, the heating element includes a warming rod 46 with an inner bus bar 48 and an outer bus wrap 50. The warming device 14d includes concentric polymer annuli with an outer conduit 52 and an inner conduit 54. The warming rod 46 is in the center of the inner conduit 54, which may be substantially sized to accommodate and support the warming rod 46. Fluid may pass through the passageways 56a and 56b. A principle advantage of this arrangement is that the heat generated by the warming rod 46 will generally radiate outward into the fluid passageways 56a and 56b. Thus, the warming rod 46 is substantially surrounded by the fluid passageways 56a and 56b, and the heat lost to the environment is minimized.

Figure 7:
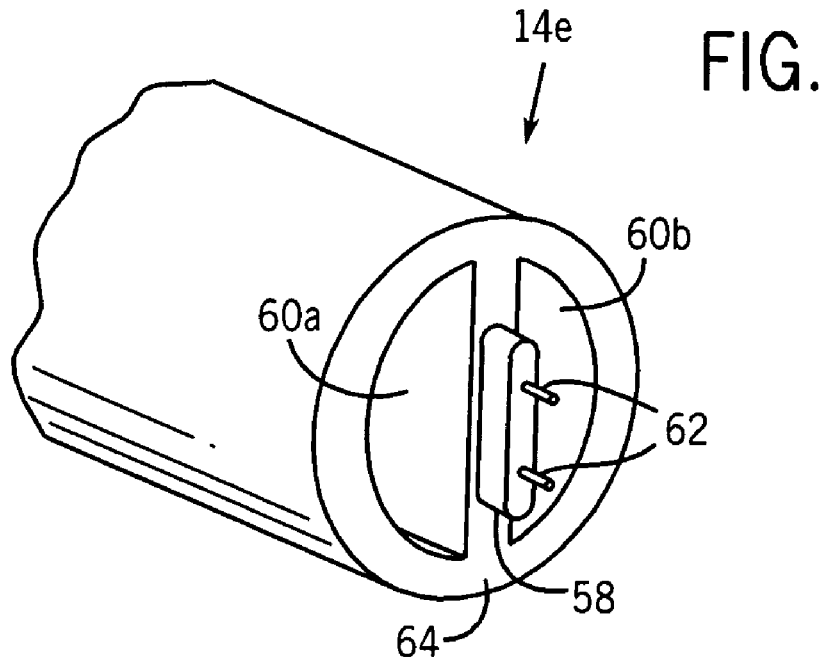
FIG. 7 illustrates a cross-sectional view of an exemplary warming device with an interior warming plate.

FIG. 7 illustrates an alternate warming device 14e in which a substantially planar warming element 58 separates fluid passageway 60a and 60b defined by a conduit 64. In this embodiment, the warming element 58 and its embedded bus wires 62 have a flat profile that increases the surface area to volume ratio between the heating element and fluid passageways 60a and 60b. The conduit 64 surrounds the warming element to define the fluid passageways 60a and 60b. Such a configuration provides the advantages of outwardly-radiating heat with a streamlined design, which may simplify manufacturing.

The warming device 14 as provided herein may be manufactured in any suitable manner, such as by extrusion, molding, casting, or dipping, for example. For example, the warming device 14a may be manufactured as a tri-layer co-extruded product wherein the warming layer 28 is sandwiched between and inner layer 22 and outer layer 26, and wherein the entire tri-layer extrusion is extruded over the conductive bus wires 32. In other embodiments, it may be advantageous to perform a two-step extrusion, whereby a positive temperature coefficient material is first extruded over bus wires or bus bars, and insulating or support layers are then extruded over the positive temperature coefficient material. In other embodiments utilizing bus wraps, such as foil wraps, it may be necessary to add manufacturing steps for wrapping the foil material over an extruded positive temperature material.

While the invention may be susceptible to various modifications and alternative forms, specific embodiments have been shown by way of example in the drawings and have been described in detail herein. However, it should be understood that the invention is not intended to be limited to the particular forms disclosed. For example, it is envisioned that the present techniques may be useful for warming non-IV medical fluids. Small volumes of fluid are sometimes used to irrigate during surgical procedures. Warmed fluids are also used during surgical preparation to keep the patient normothermic. Also, surgeons may use small volumes of warmed fluids to flush areas of tissue during surgery to prevent the conduction of cold temperatures into an open incision. Further, it is envisioned that in certain circumstances, physicians may wish to heat fluid to temperatures that deviate from normal body temperatures. For example, inducing hypothermic or hyperthermic conditions may have therapeutic benefits in certain circumstances. In those instances, physicians may wish to administer fluids at temperatures other than body temperature.

What is claimed is:

1. An apparatus comprising:
   a flexible conduit for transferring a medical fluid, wherein the conduit comprises at least one portion configured to heat the medical fluid to approximately body temperature via a positive temperature coefficient material disposed in-line along the length of the conduit, wherein the positive temperature coefficient material comprises a temperature self-regulating polymer or a resin; and
   at least one electrically conductive element disposed in or adjacent to the positive temperature coefficient material, wherein when the electrically conductive element conducts electricity, a temperature of the positive temperature coefficient material increases until body temperature is reached.

2. The apparatus of claim 1, wherein the positive temperature coefficient material comprises polyethylene, polyvinyl chloride, polyester, polyurethane, polyimide, silicon or epoxy resins.

3. The apparatus of claim 2, wherein the positive temperature coefficient material comprises a resin.

4. The apparatus of claim 1, wherein the positive temperature coefficient material has a switching temperature from about 30° C. to about 45° C.

5. The apparatus of claim 1, wherein the positive temperature coefficient material conducts substantially no current at temperatures greater than at least 50° C.

6. The apparatus of claim 1, wherein the positive temperature coefficient material comprises electrically conductive particles, fibers, or a combination thereof.

7. The apparatus of claim 1, wherein the positive temperature coefficient material comprises carbon, coated carbon, graphite, coated graphite, metal alloy, or ceramic.

8. The apparatus of claim 7, wherein the carbon comprises carbon black.

9. The apparatus of claim 1, wherein the conduit comprises an annulus diameter measured from the outermost wall ranging from 0.005 inches to 0.5 inches.

10. The apparatus of claim 1, wherein the positive temperature coefficient material comprises electrically conductive bodies in the concentration of at least 0.5% by weight.

11. The apparatus of claim 1, wherein the electrically conductive element comprises at least one electrically conductive bus wire, bus bar or bus wrap.

12. The apparatus of claim 11, wherein the positive temperature coefficient material is extruded over the electrically conductive bus wire or bus bar.

13. The apparatus of claim 11, wherein the bus wrap is disposed on the positive temperature coefficient material.

14. The apparatus of claim 1, wherein the conduit is configured so that positive temperature coefficient material forms a lumen.

15. The apparatus of claim 1, wherein the conduit is configured so that positive temperature coefficient material forms a substantially rod-shaped structure.

16. The apparatus of claim 1, wherein the conduit is configured so that positive temperature coefficient material forms a planar structure.

17. The apparatus of claim 1, comprising at least one insulating layer.

18. The apparatus of claim 17, wherein the insulating layer is extruded over the positive temperature coefficient material.

19. The apparatus of claim 17, wherein the insulating layer is co-extruded with the positive temperature coefficient material.

20. The apparatus of claim 1, wherein the medical fluid comprises whole blood, serum, plasma, a blood substitute, electrolytes, or a therapeutic compound.

21. The apparatus of claim 1, wherein the apparatus does not comprise a temperature sensor.

22. The apparatus of claim 1, wherein the fluid is visible through at least a portion of the conduit.

23. The apparatus of claim 1, wherein the positive temperature coefficient material divides the conduit into multiple passageways for the medical fluid.

24. The apparatus of claim 1, wherein the positive temperature coefficient material is disposed along a center axis of the conduit.

* * * * *

UNITED STATES PATENT AND TRADEMARK OFFICE
CERTIFICATE OF CORRECTION

| | | |
|---|---|---|
| PATENT NO. | : 7,657,163 B2 | Page 1 of 1 |
| APPLICATION NO. | : 11/527069 | |
| DATED | : February 2, 2010 | |
| INVENTOR(S) | : Paul W Martens | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Signed and Sealed this

Thirtieth Day of November, 2010

David J. Kappos
*Director of the United States Patent and Trademark Office*